US009433715B2

(12) United States Patent
Kantrowitz et al.

(10) Patent No.: US 9,433,715 B2
(45) Date of Patent: Sep. 6, 2016

(54) STABLE AORTIC BLOOD PUMP IMPLANT

(71) Applicant: L-VAD TECHNOLOGY, INC., Detroit, MI (US)

(72) Inventors: Adrian Kantrowitz, Auburn Hills, MI (US); Robert Merrill Smith, Grosse Ile, MI (US)

(73) Assignee: L-VAD Technology, Inc., Detroit, MI (US)

( * ) Notice: Subject to any disclaimer, the term of this patent is extended or adjusted under 35 U.S.C. 154(b) by 0 days.

(21) Appl. No.: 13/971,852

(22) Filed: Aug. 21, 2013

(65) Prior Publication Data
US 2014/0088340 A1 Mar. 27, 2014

Related U.S. Application Data

(63) Continuation of application No. 10/770,269, filed on Feb. 2, 2004, now Pat. No. 8,540,618.

(60) Provisional application No. 60/444,077, filed on Jan. 31, 2003, provisional application No. 60/477,740, filed on Jun. 12, 2003.

(51) Int. Cl.
*A61M 1/12* (2006.01)
*A61M 1/10* (2006.01)

(52) U.S. Cl.
CPC .............. *A61M 1/12* (2013.01); *A61M 1/1037* (2013.01); *A61M 1/1072* (2013.01); *A61M 1/122* (2014.02)

(58) Field of Classification Search
CPC .................. A61M 1/1037; A61M 2001/1043; A61M 2001/1044; A61M 1/106; A61M 1/107; A61M 1/1072
USPC ........................................................ 600/16–18
See application file for complete search history.

(56) References Cited

U.S. PATENT DOCUMENTS

| 3,585,983 | A | 6/1971 | Kantrowitz et al. | 600/18 |
|---|---|---|---|---|
| 3,698,381 | A | 10/1972 | Federico et al. | 600/17 |
| 3,720,199 | A | 3/1973 | Rishton et al. | 600/18 |
| 3,720,200 | A | 3/1973 | Laird | 600/18 |
| 3,769,960 | A | 11/1973 | Robinson | 600/18 |
| 3,939,820 | A | 2/1976 | Grayzel | 600/18 |
| 3,985,123 | A | 10/1976 | Herzlinger et al. | 600/526 |
| 4,014,317 | A | 3/1977 | Bruno | 600/18 |
| 4,016,871 | A | 4/1977 | Schiff | 600/510 |
| 4,058,855 | A | 11/1977 | Runge | 623/3.18 |
| 4,080,958 | A | 3/1978 | Bregman et al. | 600/16 |
| 4,116,589 | A | 9/1978 | Rishton | 417/384 |
| 4,195,623 | A | 4/1980 | Zeff et al. | 600/18 |
| 4,204,524 | A | 5/1980 | Martin et al. | 600/17 |
| 4,261,339 | A | 4/1981 | Hanson et al. | 600/18 |
| 4,276,874 | A | 7/1981 | Wolvek et al. | 600/18 |

(Continued)

FOREIGN PATENT DOCUMENTS

| EP | 234046 A1 | 9/1987 |
|---|---|---|
| EP | 363203 A2 | 4/1990 |
| EP | 449786 A1 | 10/1991 |

*Primary Examiner* — George Evanisko
(74) *Attorney, Agent, or Firm* — Avery N. Goldstein; Blue Filament Law

(57) ABSTRACT

An aortic blood pump is described that is secured to a patient aorta that can be inflated and deflated in response to selective communication with a source of pressurized fluid or air. An expanded stent creates an area in with the pump and inflate and deflate. A system is also detailed including the pump and an external air line external to a patient body.

13 Claims, 5 Drawing Sheets

(56) References Cited

U.S. PATENT DOCUMENTS

| | | | |
|---|---|---|---|
| 4,311,133 A | 1/1982 | Robinson | 600/18 |
| 4,314,550 A | 2/1982 | Apstein | 600/16 |
| 4,327,709 A | 5/1982 | Hanson et al. | 600/18 |
| 4,346,698 A | 8/1982 | Hanson et al. | 600/18 |
| 4,362,150 A | 12/1982 | Lombardi, Jr. et al. | 600/18 |
| 4,402,307 A | 9/1983 | Hanson et al. | 600/18 |
| 4,407,271 A | 10/1983 | Schiff | 600/17 |
| 4,422,447 A | 12/1983 | Schiff | 600/18 |
| 4,444,186 A | 4/1984 | Wolvek et al. | 606/194 |
| 4,467,790 A | 8/1984 | Schiff | 600/18 |
| 4,473,067 A | 9/1984 | Schiff | 600/18 |
| 4,515,587 A | 5/1985 | Schiff | 600/18 |
| 4,522,194 A | 6/1985 | Normann | 600/18 |
| 4,522,195 A | 6/1985 | Schiff | 600/18 |
| 4,527,549 A | 7/1985 | Gabbay | 600/18 |
| 4,531,512 A | 7/1985 | Wolvek et al. | 600/18 |
| 4,531,936 A | 7/1985 | Gordon | 604/500 |
| 4,540,404 A | 9/1985 | Wolvek | 604/103.05 |
| 4,541,417 A | 9/1985 | Krikorian | 600/17 |
| 4,546,759 A | 10/1985 | Solar | 600/18 |
| 4,552,127 A | 11/1985 | Schiff | 600/18 |
| 4,569,332 A | 2/1986 | Schiff et al. | 600/18 |
| 4,576,142 A | 3/1986 | Schiff | 600/18 |
| 4,583,523 A | 4/1986 | Kleinke et al. | 600/16 |
| 4,584,989 A | 4/1986 | Stith | 600/18 |
| 4,592,340 A | 6/1986 | Boyles | 600/18 |
| 4,630,597 A * | 12/1986 | Kantrowitz et al. | 600/18 |
| 4,644,936 A | 2/1987 | Schiff | 600/18 |
| 4,646,719 A | 3/1987 | Neuman et al. | 600/18 |
| 4,681,092 A | 7/1987 | Cho et al. | 600/18 |
| 4,685,446 A | 8/1987 | Choy | 600/18 |
| 4,697,573 A | 10/1987 | Schiff | 600/18 |
| 4,697,574 A | 10/1987 | Karcher et al. | 600/17 |
| 4,733,652 A | 3/1988 | Kantrowitz et al. | 600/18 |
| 4,741,328 A | 5/1988 | Gabbay | 600/18 |
| 4,753,221 A | 6/1988 | Kensey et al. | 600/16 |
| 4,771,765 A | 9/1988 | Choy et al. | 600/18 |
| 4,785,795 A | 11/1988 | Singh | 600/18 |
| 4,787,368 A | 11/1988 | Kageyama | 600/18 |
| 4,794,910 A | 1/1989 | Mushika | 600/18 |
| 4,804,358 A | 2/1989 | Karcher et al. | 600/17 |
| 4,809,676 A | 3/1989 | Freeman | 600/16 |
| 4,809,681 A | 3/1989 | Kantrowitz et al. | 600/17 |
| 4,813,952 A | 3/1989 | Khalafalla | 623/3.12 |
| 4,827,906 A | 5/1989 | Robicsek et al. | 600/17 |
| 4,861,330 A | 8/1989 | Voss | 600/18 |
| 4,897,077 A | 1/1990 | Cicciu et al. | 600/18 |
| 4,902,272 A | 2/1990 | Milder et al. | 600/18 |
| 4,902,273 A | 2/1990 | Choy et al. | 600/18 |
| 4,906,229 A | 3/1990 | Wampler | 600/16 |
| 4,925,443 A | 5/1990 | Heilman et al. | 600/16 |
| 4,931,036 A | 6/1990 | Kanai et al. | 600/18 |
| 4,943,275 A | 7/1990 | Stricker | 600/18 |
| 4,979,936 A | 12/1990 | Stephenson et al. | 600/16 |
| 4,985,014 A | 1/1991 | Orejola | 600/18 |
| 4,994,018 A | 2/1991 | Saper | 600/18 |
| 4,994,078 A | 2/1991 | Jarvik | 623/3.14 |
| 5,004,472 A | 4/1991 | Wallace | 606/194 |
| 5,006,104 A | 4/1991 | Smith et al. | 600/16 |
| 5,024,668 A | 6/1991 | Peters et al. | 606/194 |
| 5,045,051 A | 9/1991 | Milder et al. | 600/16 |
| 5,090,957 A | 2/1992 | Moutafis et al. | 600/18 |
| 5,092,879 A | 3/1992 | Jarvik | 623/3.3 |
| 5,116,305 A | 5/1992 | Milder et al. | 600/18 |
| 5,120,299 A | 6/1992 | Lombardi | 600/18 |
| 5,129,878 A | 7/1992 | Takano et al. | 600/18 |
| 5,135,467 A | 8/1992 | Citron | 600/16 |
| 5,158,529 A | 10/1992 | Kanai | 600/18 |
| 5,167,628 A | 12/1992 | Boyles | 604/103.07 |
| 5,169,378 A | 12/1992 | Figuera | 600/16 |
| 5,169,379 A | 12/1992 | Freed et al. | 600/18 |
| 5,171,207 A | 12/1992 | Whalen | 600/16 |
| 5,176,619 A | 1/1993 | Segalowitz | 600/18 |
| 5,195,942 A | 3/1993 | Weil et al. | 600/18 |
| 5,222,980 A | 6/1993 | Gealow | 623/3.12 |
| 5,230,692 A | 7/1993 | Kanai | 600/18 |
| 5,242,374 A | 9/1993 | Isoyama et al. | 600/18 |
| 5,254,090 A | 10/1993 | Lombardi et al. | 604/96.01 |
| 5,267,940 A | 12/1993 | Moulder | 600/16 |
| 5,273,518 A | 12/1993 | Lee et al. | 600/16 |
| 5,300,017 A | 4/1994 | Isoyama et al. | 600/18 |
| 5,300,113 A | 4/1994 | Arpesella et al. | 623/3.21 |
| 5,308,319 A | 5/1994 | Ide et al. | 600/18 |
| 5,318,501 A | 6/1994 | Lee et al. | 600/16 |
| 5,330,451 A | 7/1994 | Gabbay | 604/284 |
| 5,334,142 A | 8/1994 | Paradis | 604/509 |
| 5,344,385 A | 9/1994 | Buck et al. | 600/16 |
| 5,365,933 A | 11/1994 | Elghazzawi | 600/510 |
| 5,380,267 A | 1/1995 | Boutelle et al. | 600/18 |
| 5,409,444 A | 4/1995 | Kensey et al. | 600/18 |
| 5,411,027 A | 5/1995 | Wiklund et al. | 600/439 |
| 5,413,549 A | 5/1995 | Leschinsky | 600/18 |
| 5,413,558 A | 5/1995 | Paradis | 604/101.05 |
| 5,421,807 A | 6/1995 | Atsumi | 600/16 |
| RE34,993 E | 7/1995 | Cicciu et al. | 600/18 |
| 5,429,584 A | 7/1995 | Chiu | 600/18 |
| 5,443,504 A | 8/1995 | Hill | 623/3.12 |
| 5,453,076 A | 9/1995 | Kiyota et al. | 600/18 |
| 5,479,946 A | 1/1996 | Trumble | 128/899 |
| 5,484,385 A | 1/1996 | Rishton | 600/16 |
| 5,498,228 A | 3/1996 | Royalty et al. | 600/18 |
| 5,514,073 A | 5/1996 | Miyata et al. | 600/18 |
| 5,531,776 A | 7/1996 | Ward et al. | 607/105 |
| 5,647,380 A | 7/1997 | Campbell et al. | 128/898 |
| 5,653,676 A | 8/1997 | Buck et al. | 600/16 |
| 5,678,570 A | 10/1997 | Manning | 128/897 |
| 5,683,347 A | 11/1997 | Miyata et al. | 600/18 |
| 5,688,245 A | 11/1997 | Runge | 604/151 |
| 5,701,919 A | 12/1997 | Buck et al. | 128/898 |
| 5,711,754 A | 1/1998 | Miyata et al. | 600/18 |
| 5,716,318 A | 2/1998 | Manning | 600/16 |
| 5,718,248 A | 2/1998 | Trumble et al. | 128/899 |
| 5,722,930 A | 3/1998 | Larson, Jr. et al. | 600/16 |
| 5,755,687 A | 5/1998 | Donlon | 604/508 |
| 5,758,664 A | 6/1998 | Campbell et al. | 128/898 |
| 5,759,148 A | 6/1998 | Sipin | 600/18 |
| 5,772,631 A | 6/1998 | Lepor | 604/96.01 |
| 5,817,001 A | 10/1998 | Leschinsky et al. | 600/18 |
| 5,820,542 A * | 10/1998 | Dobak, III et al. | 600/16 |
| 5,827,171 A | 10/1998 | Dobak, III et al. | 600/16 |
| 5,848,962 A | 12/1998 | Feindt et al. | 600/16 |
| 5,865,721 A | 2/1999 | Andrews et al. | 600/18 |
| 5,888,186 A | 3/1999 | Trumble et al. | 600/16 |
| 5,910,103 A | 6/1999 | Saper et al. | 600/18 |
| 5,913,814 A | 6/1999 | Zantos | 600/18 |
| 5,928,132 A | 7/1999 | Leschinsky | 600/16 |
| 5,980,448 A | 11/1999 | Heilman et al. | 600/16 |
| 5,984,857 A | 11/1999 | Buck et al. | 600/16 |
| 6,004,258 A | 12/1999 | Watari et al. | 600/18 |
| 6,007,479 A | 12/1999 | Rottenberg et al. | 600/16 |
| 6,024,693 A | 2/2000 | Schock et al. | 600/18 |
| 6,030,335 A | 2/2000 | Franchi | 600/16 |
| 6,030,336 A | 2/2000 | Franchi | 600/18 |
| 6,042,532 A | 3/2000 | Freed et al. | 600/18 |
| 6,045,496 A | 4/2000 | Pacella et al. | 600/16 |
| 6,050,932 A | 4/2000 | Franchi | 600/16 |
| 6,056,723 A | 5/2000 | Donlon | 604/102.01 |
| 6,060,454 A | 5/2000 | Duhaylongsod | 514/26 |
| 6,066,085 A | 5/2000 | Heilman et al. | 600/16 |
| 6,083,260 A | 7/2000 | Aboul-Hosn | 623/3.14 |
| 6,087,394 A | 7/2000 | Duhaylongsod | 514/478 |
| 6,090,096 A | 7/2000 | St. Goar et al. | 604/509 |
| 6,120,431 A | 9/2000 | Magovern et al. | 600/17 |
| 6,127,410 A | 10/2000 | Duhaylongsod | 514/478 |
| 6,132,363 A | 10/2000 | Freed et al. | 600/16 |
| 6,132,364 A | 10/2000 | Rottenberg et al. | 600/16 |
| 6,136,025 A * | 10/2000 | Barbut et al. | 623/3.1 |
| 6,149,578 A | 11/2000 | Downey et al. | 600/18 |
| 6,179,793 B1 | 1/2001 | Rothman et al. | 601/44 |
| 6,190,304 B1 | 2/2001 | Downey et al. | 600/18 |
| 6,191,111 B1 | 2/2001 | Leschinsky | 514/12 |
| 6,200,260 B1 | 3/2001 | Bolling | 600/16 |
| 6,210,318 B1 * | 4/2001 | Lederman | 600/18 |
| 6,210,319 B1 | 4/2001 | Williams et al. | 600/18 |

(56) References Cited

U.S. PATENT DOCUMENTS

| | | | |
|---|---|---|---|
| 6,228,018 B1 | 5/2001 | Downey et al. | 600/18 |
| 6,231,498 B1 | 5/2001 | Pfeiffer et al. | 600/18 |
| 6,241,706 B1 | 6/2001 | Leschinsky et al. | 604/99.01 |
| 6,245,008 B1 | 6/2001 | Leschinsky et al. | 600/16 |
| 6,290,641 B1 | 9/2001 | Nigroni et al. | 600/18 |
| 6,296,605 B1 | 10/2001 | Michelman et al. | 600/16 |
| 6,299,575 B1 | 10/2001 | Bolling | 600/16 |
| 6,387,037 B1 | 5/2002 | Bolling et al. | 600/16 |
| 6,390,969 B1 | 5/2002 | Bolling et al. | 600/16 |
| 6,398,715 B1 | 6/2002 | Magovern et al. | 600/16 |
| 6,406,422 B1 | 6/2002 | Landesberg | 600/17 |
| 6,414,018 B1 | 7/2002 | Duhaylongsod | 514/478 |
| 6,423,031 B1 | 7/2002 | Donlon | 604/102.01 |
| 6,428,464 B1 | 8/2002 | Bolling | 600/16 |
| 6,440,059 B1 | 8/2002 | Haas et al. | 600/17 |
| 6,468,200 B1 | 10/2002 | Fischi | 600/18 |
| 6,471,633 B1 * | 10/2002 | Freed | 600/16 |
| 6,511,412 B1 | 1/2003 | Freed et al. | 600/17 |
| 6,511,413 B2 | 1/2003 | Landesberg | 600/17 |
| 6,514,226 B1 | 2/2003 | Levin et al. | 604/9 |
| 6,532,964 B2 | 3/2003 | Aboul-Hosn et al. | 128/898 |
| 6,536,260 B2 | 3/2003 | Williams | 73/40 |
| 6,547,821 B1 | 4/2003 | Taylor et al. | 623/3.1 |
| 6,585,635 B1 | 7/2003 | Aldrich | 600/16 |
| 6,610,004 B2 | 8/2003 | Viole et al. | 600/16 |
| 6,616,597 B2 | 9/2003 | Schock et al. | 600/18 |
| 6,616,598 B2 | 9/2003 | Kaushansky et al. | 600/16 |
| 6,632,169 B2 | 10/2003 | Korakianitis et al. | 600/16 |
| 6,666,814 B2 | 12/2003 | Downey et al. | 600/18 |
| 6,669,624 B2 | 12/2003 | Frazier | 600/18 |
| 6,679,829 B2 | 1/2004 | Nigroni et al. | 600/18 |
| 6,685,621 B2 | 2/2004 | Bolling et al. | 600/16 |
| 6,709,383 B2 | 3/2004 | Tsukahara et al. | 600/16 |
| 6,711,436 B1 | 3/2004 | Duhaylongsod | 607/9 |
| 6,735,532 B2 | 5/2004 | Freed et al. | 702/50 |
| 6,800,068 B1 | 10/2004 | Dae et al. | 604/113 |
| 6,808,484 B1 | 10/2004 | Peters et al. | 600/16 |
| 6,827,682 B2 | 12/2004 | Bugge et al. | 600/16 |
| 6,863,648 B2 | 3/2005 | Williams et al. | 600/18 |
| 2001/0016676 A1 | 8/2001 | Williams et al. | 600/18 |
| 2001/0031907 A1 | 10/2001 | Downey et al. | 600/18 |
| 2001/0034469 A1 | 10/2001 | Nigroni et al. | 600/18 |
| 2001/0037048 A1 | 11/2001 | Pfeiffer et al. | 600/18 |
| 2002/0002321 A1 | 1/2002 | Tsukahara et al. | 600/16 |
| 2002/0045795 A1 | 4/2002 | Aboul-Hosn et al. | 600/16 |
| 2002/0072647 A1 | 6/2002 | Schock et al. | 600/16 |
| 2002/0103413 A1 | 8/2002 | Bugge et al. | 600/16 |
| 2002/0137981 A1 | 9/2002 | Williams et al. | 600/18 |
| 2002/0151761 A1 | 10/2002 | Viole et al. | 600/16 |
| 2002/0173693 A1 | 11/2002 | Landesberg | 600/16 |
| 2002/0198436 A1 | 12/2002 | Hoshino | 600/18 |
| 2003/0023131 A1 | 1/2003 | Antaki | 600/16 |
| 2003/0032853 A1 | 2/2003 | Korakianitis et al. | 600/16 |
| 2003/0055309 A1 | 3/2003 | Kaushansky et al. | 600/18 |
| 2003/0069466 A1 | 4/2003 | Tsukahara et al. | 600/16 |
| 2003/0069468 A1 | 4/2003 | Bolling et al. | 600/16 |
| 2003/0083539 A1 | 5/2003 | Leschinsky | 600/18 |
| 2003/0088147 A1 | 5/2003 | Bolling et al. | 600/18 |
| 2003/0092961 A1 | 5/2003 | Korakianitis et al. | 600/16 |
| 2003/0097036 A1 | 5/2003 | St. Germain et al. | 600/16 |
| 2003/0105383 A1 | 6/2003 | Barbut et al. | 600/16 |
| 2003/0125601 A1 | 7/2003 | Schock et al. | 600/18 |
| 2003/0135086 A1 | 7/2003 | Khaw et al. | 600/16 |
| 2003/0144624 A1 | 7/2003 | Barbut | 604/8 |
| 2003/0171642 A1 | 9/2003 | Schock et al. | 600/18 |
| 2003/0176760 A1 | 9/2003 | El Oakley et al. | 600/16 |
| 2003/0191357 A1 | 10/2003 | Frazier | 600/16 |
| 2003/0195382 A1 | 10/2003 | Barbut | 600/16 |
| 2003/0233023 A1 | 12/2003 | Khaghani et al. | 600/18 |
| 2004/0015043 A1 | 1/2004 | Frazier | 600/18 |
| 2004/0019251 A1 | 1/2004 | Viole et al. | 600/16 |
| 2004/0034272 A1 | 2/2004 | Diaz et al. | 600/18 |
| 2004/0059179 A1 | 3/2004 | Maguire et al. | 600/16 |
| 2004/0059183 A1 | 3/2004 | Jansen et al. | 600/17 |
| 2004/0064090 A1 | 4/2004 | Keren et al. | 604/96.01 |
| 2004/0064091 A1 | 4/2004 | Keren et al. | 604/96.01 |
| 2004/0073080 A1 | 4/2004 | Peters et al. | 600/18 |
| 2004/0092789 A1 | 5/2004 | Tsukahara et al. | 600/16 |
| 2004/0097782 A1 | 5/2004 | Korakianitis et al. | 600/16 |
| 2004/0097783 A1 | 5/2004 | Peters et al. | 600/16 |
| 2004/0097784 A1 * | 5/2004 | Peters et al. | 600/18 |
| 2004/0116768 A1 | 6/2004 | Bolling et al. | 600/16 |
| 2004/0122282 A1 | 6/2004 | Anzellini | 600/16 |
| 2004/0147803 A1 | 7/2004 | Hegde et al. | 600/16 |
| 2004/0152945 A1 | 8/2004 | Kantrowitz et al. | 600/18 |
| 2004/0167376 A1 | 8/2004 | Peters et al. | 600/18 |
| 2004/0230090 A1 | 11/2004 | Hegde et al. | 600/18 |
| 2004/0236172 A1 | 11/2004 | Bolling et al. | 600/16 |
| 2004/0236173 A1 | 11/2004 | Viole et al. | 600/16 |
| 2004/0267086 A1 | 12/2004 | Anstadt et al. | 600/17 |
| 2005/0020870 A1 | 1/2005 | Suzuki et al. | 600/16 |
| 2005/0043579 A1 | 2/2005 | Dae et al. | 600/16 |
| 2005/0049451 A1 | 3/2005 | Schock et al. | 600/18 |
| 2005/0070755 A1 | 3/2005 | Zheng et al. | 600/16 |
| 2005/0075531 A1 | 4/2005 | Loeb et al. | 600/17 |
| 2005/0085685 A1 | 4/2005 | Barbut | 600/16 |
| 2005/0124849 A1 | 6/2005 | Barbut et al. | 600/18 |

* cited by examiner

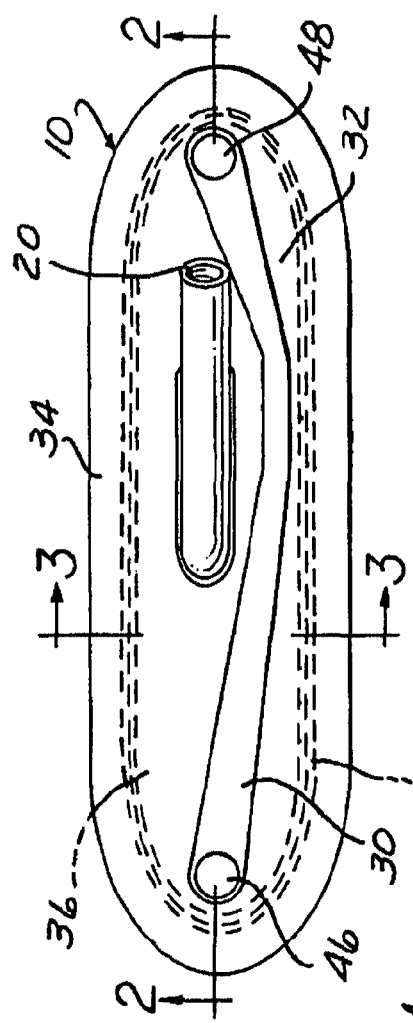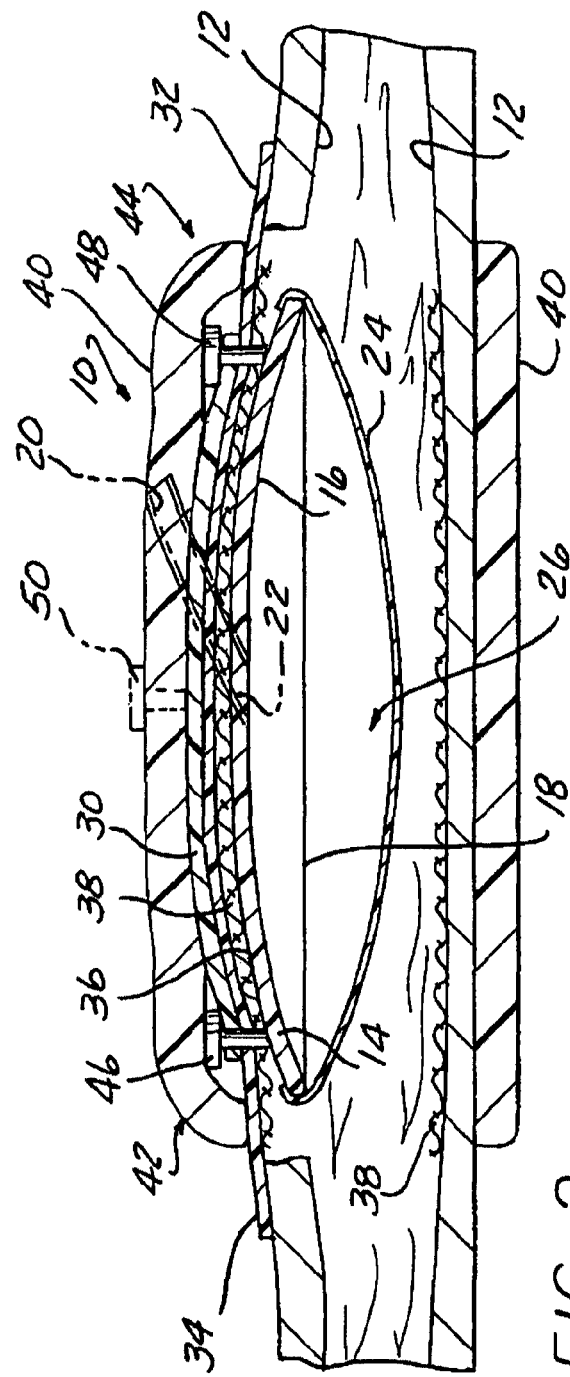
FIG. 1
FIG. 2

STABLE AORTIC BLOOD PUMP IMPLANT

REFERENCE TO RELATED APPLICATIONS

This application is a continuation of U.S. Utility application Ser. No. 10/770,269 filed Feb. 2, 2004, now U.S. Pat. No. 8,540,618 B2 that in turn claims priority benefit to U.S. provisional application Ser. No. 60/444,077, filed Jan. 31, 2003, and to U.S. provisional application Ser. No. 60/477,740, filed Jun. 11, 2003, the entire contents of the aforementioned applications are hereby incorporated herein by reference.

FIELD OF THE INVENTION

The present invention relates generally to an implantable cardiac blood pump and in particular to an implantable blood pump including a structure adapted to maintain implant stability.

BACKGROUND OF THE INVENTION

Heart disease is one of the leading causes of death for elderly people. Currently, medical science cannot reverse the damage done to the cardiac muscle by heart disease. The only known solution is a heart transplant. However, the number of cardiac patients in need of a heart transplant far exceeds the limited supply of donor hearts available.

The scarcity of human hearts available for transplant, as well as the logistics necessary to undertake heart transplant surgery, make a permanently implantable cardiac assist device the only viable option for many heart patients. An aortic blood pump can be permanently surgically implanted in the wall of the aorta to augment the pumping action of the heart. The aortic blood pump is sometimes referred to as a mechanical auxiliary ventricle assist device, dynamic aortic patch, or permanent balloon pump. Alternatively, the aortic blood pump can be inserted endoscopically, and is sometimes referred to as a temporary balloon pump, or simply as a balloon pump, since extended periods of use are possible depending on the method and location of surgical insertion.

Typically, the aortic blood pump includes a flexible bladder to be inflated and deflated in a predetermined synchronous pattern with respect to the diastole and systole of the patient to elevate aortic blood pressure immediately after aortic valve closure. Inflation and deflation of the bladder can be accomplished by means of a supply tube connected to the bladder and can be connected to a percutaneous access device (PAD). The PAD can be permanently surgically implanted in a patient's body to provide a through-the-skin coupling for connecting the supply tube to an extra-corporeal fluid pressure source. Electrical leads from electrodes implanted in the myocardium are likewise brought out through the skin by means of the PAD. The "R" wave of the electrocardiograph can be employed to control the fluid pressure source to inflate and deflate the inflatable chamber in a predetermined synchronous relationship with the heart action.

The aortic blood pump acts to assist or augment the function of the left ventricle and is typically restricted to use in patients who have some functioning myocardium. The aortic blood pump does not need to be operated full time, and in fact, can be operated periodically on a scheduled on-time, off-time regimen. Typically, the patient can be at least temporarily independent of the device for periods of one to four hours or more, since the aortic blood pump does not require continuous operation.

U.S. Pat. No. 6,471,633 discloses a dynamic aortic patch with an elongate bladder having a semi-rigid shell body portion and a relatively thin membrane portion defining an inflatable chamber. At least one passage extends through the shell body defining an opening in the inner surface of the shell body. The flexible membrane can be continuously bonded to the shell body adjacent the peripheral side edge to define the enclosed inflatable chamber in communication with the passage. The membrane has a reduced waist portion defining a membrane tension zone adjacent to the opening of the passage into the chamber to prevent occluding the entrance while deflating the chamber. An outer layer can be bonded to the outer side of the semi-rigid wall portion of the aortic blood pump and cut with a freely projecting peripheral edge portion to provide a suture flange for suturing the aortic blood pump in place within an incision in the aorta.

While conventional aortic balloon pumps are well known to the art, a stable aortic blood pump implant is desirable. For example, the constant movement of blood, movement of the vessel wall and the movement of the pump itself can result in deformation of the pump and vessel damage at blood/pump and vessel/pump interface area. There is a continuing need for an aortic blood pump including a structure adapted to maintain implant stability.

Particularly needed is an aortic blood pump including a structure adapted to maintain implant stability by resisting deformation in the face of the fluid and mechanical forces to which it is exposed. Thus, it would be desirable to have an aortic blood pump with a stiffening element for resisting bending and/or flexure of the shell body portion.

Additionally, the surgical implantation of a cardiac assist device is generally complicated by suturing a pump with a generally linear shape onto a curved human aorta. Thus, there exists a need for an aortic blood pump including a structure adapted to maintain implant stability by accommodation of human aortic anatomy.

SUMMARY OF THE INVENTION

An implantable aortic blood pump is described that includes a wall adapted to maintain stability of the implantable aortic blood pump when implanted, an expandable membrane attached to the wall, and an interior volume defined by the wall and the membrane. A provided pump also includes an inflation port housing integral with the wall, the inflation port housing having an aperture therein in fluid communication with the interior volume.

In one embodiment of an inventive pump, the wall is adapted to maintain implant stability by connection to an element for stiffening the wall. Illustrative elements for stiffening the wall include a stent, a brace, a stiffener or any combination thereof.

In another embodiment of an implantable aortic blood pump according to the invention, the wall is adapted to maintain implant stability by configuring the interior volume to generally follow the contour of the native human aorta.

In a preferred embodiment of the present invention, an aortic blood pump includes an elongate semi-rigid shell member having a concave inner surface and a flexible membrane integrally bonded to the outer peripheral surface of the shell member to define a chamber between the concave inner surface and the membrane, and a stiffening element for stiffening the shell member to resist bending and/or flexure. A stiffening element can include a stent, a brace, a stiffener, or any combination thereof.

An aortic blood pump according to the present invention assists cardiac function during a cardiac cycle of a patient when positioned with respect to an aorta of the patient. The aortic blood pump includes an elongate semi-rigid shell having a contoured, concave inner surface terminating at a peripheral side edge. At least one passage extends through the shell to define an opening in the inner surface. A flexible membrane can be continuously bonded to the shell adjacent the peripheral side edge to define an enclosed inflatable chamber in communication with the passage. An inventive pump optionally includes a stent. The stent is optionally partially embedded in the shell and/or can be connected to the outer surface of the semi-rigid shell to be extending outwardly from the shell to define a substantially open cylindrical area for expansion of the flexible membrane when inflated. The stent is optionally movable between an expanded position and a retracted position. The retracted position of the stent can reduce the overall dimensions of the stent to facilitate minimally invasive surgical implantation. When properly positioned within the aorta, the stent can be expanded to define the substantially open cylindrical area encompassing the zone of inflation of the flexible membrane within the aorta. Alternatively, an inflatable balloon pump can be supported by being suspended within a central portion of a collapsed or retracted stent for endoscopic surgical positioning with respect to the aorta of the patient during a minimally invasive surgical implantation. After expansion of the stent in an endoscopically selected location of the aorta, the inflatable balloon pump can be cyclically inflated and deflated to assist the cardiac function based on measured clinical parameters of the patient.

Alternatively, or additionally, the stiffening element can include a brace. Opposite ends of an elongate brace can be connected to the semi-rigid shell adjacent longitudinally extending peripheral sides to encircle the outer wall of an aorta. Alternatively, or additionally, the stiffening element can include a stiffener. Opposite ends of an elongate stiffener can be connected to the outer surface of the semi-rigid shell adjacent to opposite longitudinal ends of the shell.

Further provided is an implantable blood pump including a wall having a top surface, a bottom surface and a thickness, the wall defining an interior pump volume. The interior pump volume generally follows the contour of a native human aorta. Also included is an inflatable membrane sealed to the wall.

Optionally, the bottom surface is secured to the native human aorta. A provided pump optionally further includes a gas port housing integral with the wall. The gas port housing includes an aperture in fluid communication with the interior pump volume. The aperture defines an angle relative to the wall of between 5 and 30 degrees. The top surface of the wall is optionally overlayered with a non-tissue adhesive substance. In a further option, the thickness of the wall is variable.

An additional embodiment of a pump according to the present invention includes a wall curving to generally follow the contour of a native human aorta and an inflatable membrane sealed to the wall to form a bladder having an aperture extending from the bladder into an extra-aortic region. The pump optionally includes a patch anchoring the bladder within a human aorta. The wall optionally has less elasticity than the membrane.

A cardiac assist system is additionally provided. An inventive system includes an implantable blood pump as described herein, including an inflatable membrane sealed to a wall to form a bladder having an aperture extending from the bladder into an extra-aortic region and a gas tube affording fluid communication between the blood pump and the region external to a patient body. An inventive system optionally includes a percutaneous access device intermediate between the gas tube and the exterior of the patient's body. Further optionally included is a compressor for delivering a pulsatile gas flow, an energy source, an air tank, and electronics necessary to control the operation of the system. A gas tube communicating air to the pump is another option.

BRIEF DESCRIPTION OF THE DRAWINGS

The description herein makes reference to the accompanying drawings wherein like reference numerals refer to like parts throughout the several views, and wherein:

FIG. 1 is a plan view of an aortic blood pump with a stiffening element according to the present invention;

FIG. 2 is a cross-sectional view taken as shown in FIG. 1 illustrating the aortic blood pump in an inflated position and sutured to the wall of an aorta of a patient;

DETAILED DESCRIPTION OF THE INVENTION

Figure 3:
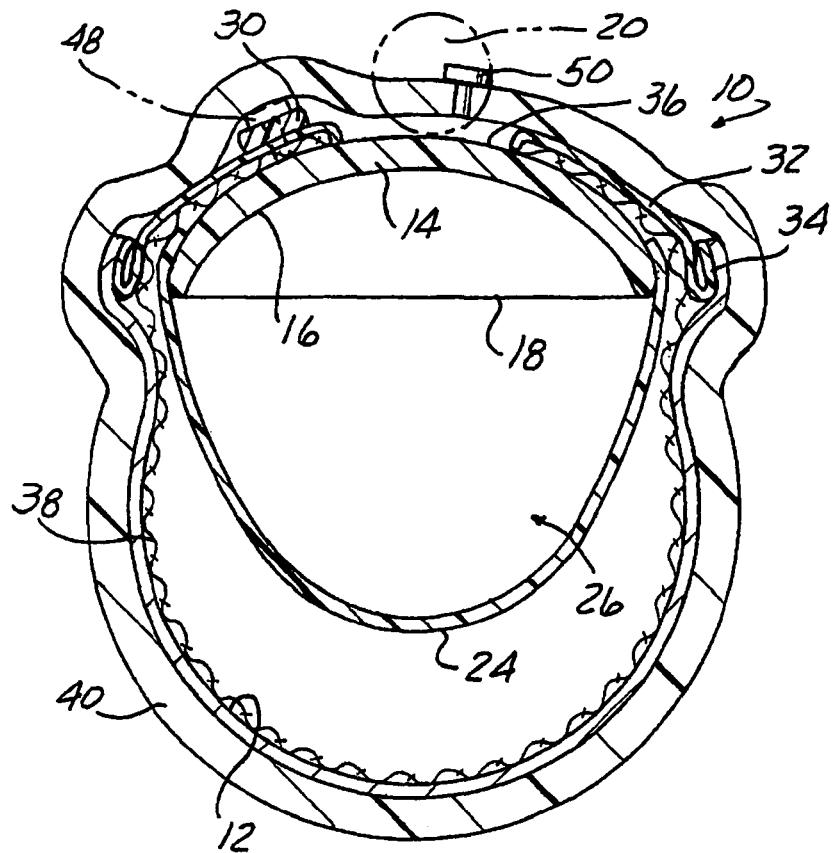
FIG. 3 is a cross section view taken as shown in FIG. 1 illustrating the aortic blood pump in the inflated condition.

A pump and a cardiac assist system according to the present invention each have utility to increase blood ejection from a compromised heart. An implantable aortic blood pump provided by the present invention includes a wall adapted to maintain stability of the implantable aortic blood pump when implanted, an expandable membrane attached to the wall; and an interior volume defined by the wall and the membrane.

In one embodiment of an inventive pump, the wall is adapted to maintain implant stability by connection to an element for stiffening the wall.

In another embodiment of an implantable aortic blood pump according to the invention, the wall is adapted to maintain implant stability by configuring the interior volume to generally follow the contour of the native human aorta.

An aortic blood pump, or permanent blood pump, generally designated as 10 is illustrated in FIGS. 1-4. The aortic blood pump 10 according the present invention assists in cardiac function during a cardiac cycle of a patient when positioned with respect to an aorta 12. The aortic blood pump 10 preferably includes an elongate, semi-rigid shell 14 having a contoured, concave inner surface 16 terminating at a peripheral side edge 18. At least one passage 20 extends through the shell 14 to define an opening 22 in the inner surface 16. An elongate, flexible membrane 24 can be continuously bonded to the shell 14 adjacent to the peripheral side edge 18. The flexible membrane 24 in cooperation with the shell 14 defines an enclosed inflatable chamber 26 in fluid communication with the passage 20.

A piece of sheet material 32 of a commercially available type and certified for use in implanted devices, or other suitable material, can be bonded to one side of the shell 14. The sheet material 32 can be cut generously to provide a peripheral hem or flange 34. The flange 34 projects freely from the shell 14 to provide a suture flange for implanting the device in an incision in the aorta 12. As previously indicated, the inflatable chamber 26 can be formed with an integral projecting tube portion or passage 20 with a distal end connected to one end of a supply tube (not shown).

Further details regarding the structure and function of the aortic blood pump and associated devices and controls can be obtained from U.S. Pat. No. 6,511,412 issued Jan. 28, 2003; U.S. Pat. No. 6,471,633 issued Oct. 29, 2002; U.S. Pat. No. 6,132,363 issued Oct. 12, 2000; U.S. Pat. No. 5,904,666 issued May 18, 1999; U.S. Pat. No. 5,833,655 issued Nov. 11, 1998; U.S. Pat. No. 5,833,619 issued Nov. 10, 1998; U.S. Pat. No. 5,242,415 issued Sep. 7, 1993; U.S. Pat. No. 4,634,422 issued Jan. 6, 1987; and U.S. Pat. No. 4,630,597 issued Dec. 23, 1986 which are incorporated by reference in their entirety herein.

Referring now to FIGS. 2-3, the pump 10 is shown in longitudinal and transverse cross-sectional views implanted within the wall of the thoracic aorta 12. The inflatable chamber 26 of the pump 10 is illustrated in an inflated condition in FIGS. 2 and 3. To implant the device, a surgeon makes a longitudinal incision through the wall of the aorta 12, usually downwardly from a location just below the subclavian artery, and the device can be placed within the incision and sewn firmly in position by sutures passing through the projecting suture flange 34 of the sheet material layer 32. The device can be implanted with minimally invasive surgical procedures and techniques. The material 32, such a Dacron, has a fibrous surface allowing migration into and mechanically interweaving of body tissues to augment the sealing action initially established by the sutures.

As can be seen in the cross-sectional views of FIGS. 2-3, the outer side of the pump 10 as implanted can be a relatively thick, semi-rigid body or shell 14 molded from a biocompatible urethane material or any suitable substitute. The shell 14 includes the projecting passage 20 formed integrally with the shell 14. As can best be seen in the plan view of FIG. 1, the shell 14 can have an elongate elliptical shape with an upper or outer surface 36 convex in both longitudinal and transverse directions. The lower or inner surface 16 of shell 14 can be concave in both the longitudinal and transverse directions. Preferably, the peripheral side edge 18 can be smoothly rounded throughout an entire extent.

The thin wall, flexible membrane 24 can be fixedly secured to the shell 14. The flexible membrane 24 can preferably be fixedly secured with respect to the outer surface 36 adjacent the peripheral side edge 18. Preferably, the membrane 24 can be free from the peripheral side edge 18 and free from the inner surface 16 of the shell 14. For purposes of illustration, membrane 24 and shell 14 are illustrated as if separately formed. Preferably, the inflatable chamber 26 can be formed by known techniques, such as solvation bonding, resulting in the membrane 24 and the shell 14 becoming in effect a single unitary structure.

As is described in greater detail in the prior patents incorporated herein by reference in their entirety, a tube (not shown) can be led from the implanted pump to a percutaneous access device implanted beneath and projecting through a patient's skin. The percutaneous access device allows the tube and, preferably, electrocardiograph leads, to be operatively connected to or disconnected from an external pump and controller. In operation, the inflatable chamber 26 can be cyclically inflated and deflated with a pressurized gaseous fluid synchronously with a heartbeat of the patient. Preferably, the synchronous cyclical inflation and deflation can be based on a set of programmable patient parameters relating to heart function.

Referring to FIGS. 1-4, the bladder includes a shell or body 14, a relatively thin membrane 24 and a Dacron or other suitable outer layer 32. The Dacron velour or other suitable material layer 32 can be bonded to the outer surface 36 of the body 14 to provide a freely projecting flange 34 used for suturing the device in place after an incision has been made in the aorta 12. The body 14 can be a relatively thick, semi-rigid shell member 14. The shell member 14 can be molded from a biocompatible urethane material and incorporates a projecting air inlet tube 20.

FIGS. 1-3 show an aortic blood pump including illustrative types of structures adapted to maintain implant stability by resisting deformation in the face of the fluid and mechanical forces to which it is exposed. In particular, a first such structure is a stent 38, composed of a wire-mesh material, in the expanded state adjacent to the wall of an aorta 12. FIG. 2 shows this in a cross-sectional view illustrating the body shape as having a convex outer surface 36 with a concave inner surface 16 extending over the full length of the body 14. The cross-sectional view of FIG. 2 illustrates the body or shell 14 with a peripheral side edge 18 tapering at both ends to approximate the geometrical intersection of the body with a substantially cylindrical aorta 12 in a saddle-like configuration. The stent 38 can be attached to the outer surface 36 of the shell 14 and extends outwardly to define a substantially open cylindrical area for expansion of the flexible membrane 24.

Further shown is another illustrative type of structure adapted to maintain implant stability, at least one elongate arcuate brace 40, which can be molded from a biocompatible urethane material for attachment to the shell or formed integrally with the shell. The brace 40 can be used alone or in combination with the stent 38. Opposite ends 42, 44 of the elongate brace 40, as shown in FIG. 2, can be connected to the outer surface 36 of the semi-rigid shell 14 to encircle an aorta 12, such that the aorta 12 can be interposed between the brace 40 and the stent 38. By way of example and not limitation, the brace 40 can be connected adjacent one longitudinal end with a living hinge allowing pivoting movement of the brace 40 with respect to the shell 14. The opposite end of the brace 40 can be connected to the shell with any suitable type of mechanical connection. By way of example and not limitation, the mechanical connection can be accomplished with an interlocking latch, a heat-stake pin, a screw, or any other suitable fastener known to those skilled in the art.

Figure 4:
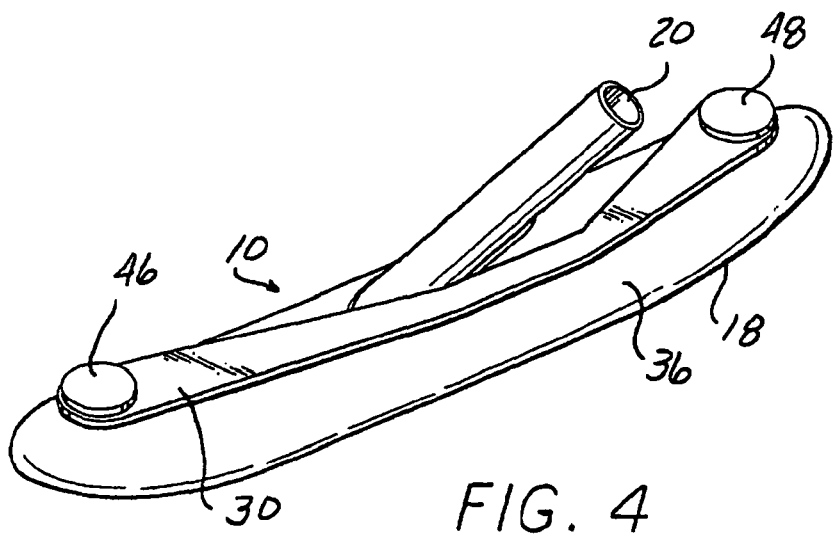
FIG. 4 is a perspective view of the blood pump or aortic blood pump with an attached stiffener according to the present invention.

An additional illustrative type of structure adapted to maintain implant stability by resisting deformation in the face of the fluid and mechanical forces to which it is exposed is shown in FIGS. 1-3. In particular, FIG. 1 shows a plan view of the body 14 and illustrates an elongate elliptical shape with a stiffener 30 attached thereto. FIGS. 2-3 also depict an elongate stiffener 30. The elongate stiffener can be molded from a biocompatible urethane material. The elongate stiffener can be formed integral with the shell or can be connected to the outer surface 36 of the semi-rigid shell 14. FIG. 2 shows the stiffener 30 in continuous contact with the shell 14 and opposite ends 42, 44 of the stiffener connected to the shell 14 with two pins 46, 48. The stiffener 30 can be connected to the shell in any suitable manner known to those skilled in the art. By way of example and not limitation, the pins 46, 48 can be in the form of heat-stake pins for attaching the stiffener to the shell in response to application of heat to the outer end of each pin 46, 48 causing the outer end of each pin 46, 48 to melt forming an enlarged head for holding the stiffener with respect to the shell 14. FIGS. 2 and 3 further illustrate a pin 50 to further secure the brace 40 within the inventive pump 10. The illustrated embodiment in FIG. 4 shows the stiffener 30 having an arcuate or angled V-shape.

Figure 5:
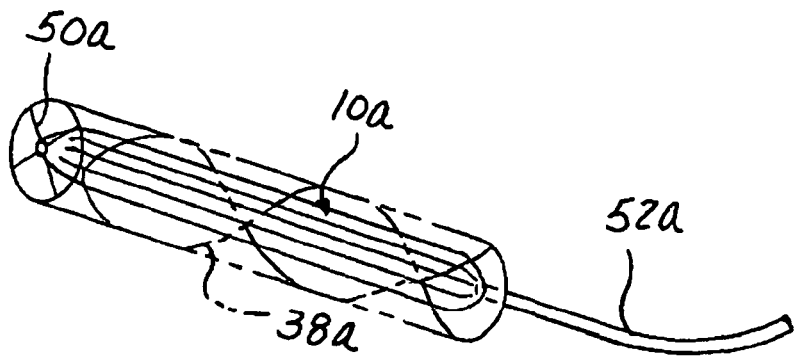
FIG. 5 is a simplified perspective view of an aortic blood pump formed as a deflated balloon pump suspended within a contracted stent prior to surgical location within an aorta of a patient.
Figure 6:
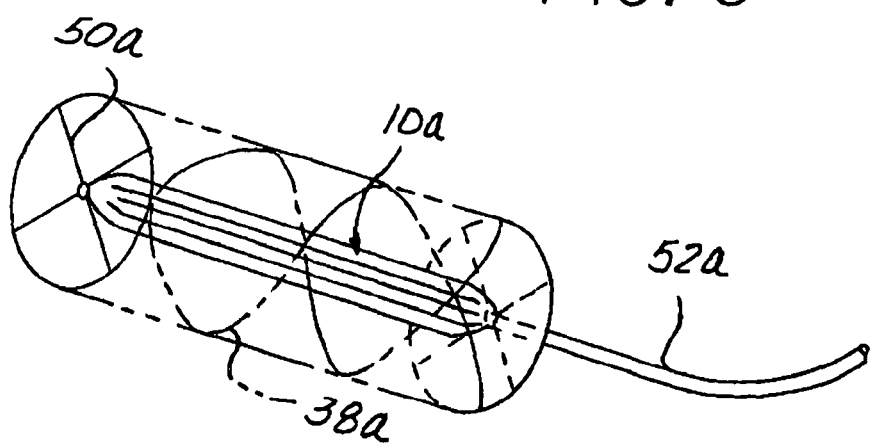
FIG. 6 is a simplified perspective view of the blood pump of FIG. 5 with the stent expanded and the balloon pump in a deflated state.
Figure 7:
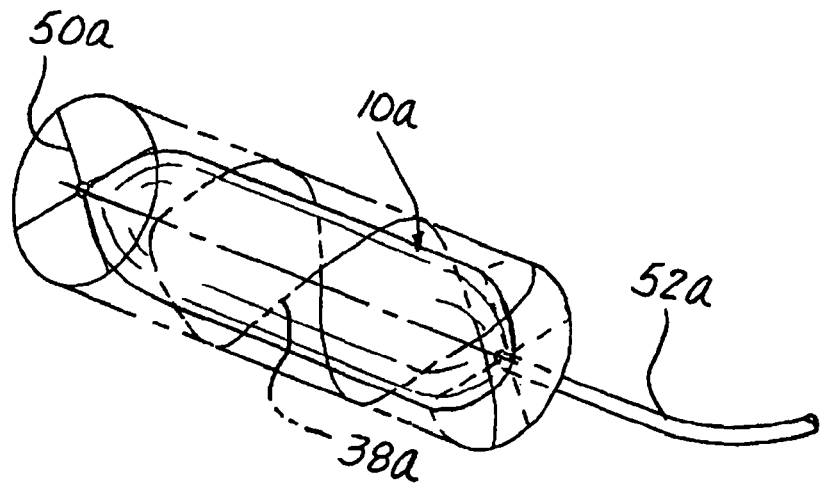
FIG. 7 is a simplified perspective view of the blood pump of FIG. 5 with the stent expanded and the balloon pump in an inflated state.

Referring now to FIGS. 5-7, a simplified perspective view of an aortic blood pump 10 formed as a balloon pump suspended within a central portion of a stent 38a is shown. The stent 38a is in a contracted or collapsed position as illustrated in FIG. 5 with the balloon pump 10a in a deflated state. The retracted position of the stent 38a and the deflated state of the balloon pump 10a allow the endoscopic surgical positioning of the stent with respect to the aorta of a patient using any known surgical technique selected from a known variety of incision locations on the patient. The implantation is performed with a minimally invasive surgical procedure or technique. After the stent 38a has been properly positioned at the desired location within the aorta of the patient, the stent 38a is expanded to engage the inner wall of the aorta (not shown) as illustrated in FIG. 6. As can best be seen in FIG. 6, the balloon pump 10a, while still in a deflated state, remains suspended in the expanded central portion of the stent by any suitable connectors 50a or attachment known to those skilled in the art of stent design and operation. The balloon pump 10a can then be cyclically inflated and deflated through flexible tube 52a synchronously with the heartbeat of the patient to assist cardiac function in response to measured clinical parameters of the patient as described in detail in the above-listed patents incorporated by reference in their entirety herein.

FIGS. 8-11 show an aortic blood pump including an illustrative structure adapted to maintain implant stability by accommodation of human aortic anatomy. An inventive blood pump as detailed in one embodiment is adapted to conform to the geometry of the human aorta. Referring now to the FIGS. 8-10, an embodiment of an inventive blood pump is shown generally at 110. The blood pump 110 is affixed to a human aorta A. In order to accommodate the blood pump 110, a portion of the aorta wall is excised and the blood pump 110 sutured thereto. The pump 110 has a generally elliptical bottom surface 112. The wall 114 terminates at the top surface 116. A line of sutures 118 serves to secure an inventive pump 110 to the aorta A. It is appreciated that conventional biocompatible tissue adhesives used to glue tissues, such as isocyanate and curable proteinaceous materials, are also operative herein to seal an inventive pump 110 to the aorta A. A gas port housing 120 is integral with the wall 114. The gas port housing 120 has an aperture 122 in fluid communication between the extra-aortic space and the interior pump volume 124. Preferably, the air port housing 120 is contoured into the pump 110 to eliminate voids where body fluids may pool. The aperture 122 defines an angle 124 relative to the wall 114. The angle 124 varies depending on the relative position of a connecting gas tube 136. Typically, the angle 124 is between 10 and 30 degrees. A membrane forms a gas-tight seal with the interior of the wall 114. The membrane 126 inflates when the gas pressure within the interior pump volume 125 exceeds the blood pressure within the aorta A.

An inventive blood pump 110, or as described elsewhere herein, is constructed from any number of biocompatible materials suitable for surgical implantation. Biocompatible materials operative herein illustratively include polyurethane, fluoropolymers, polyamides, steel, titanium, nitinol, and glass. The choice of material is dictated by the desired pump stiffness. It is appreciated that whereas a more flexible biocompatible material facilitates surgical implantation, the stiffness of the pump must be sufficient to ensure it maintains its intended geometry once implanted.

Optionally, the top surface 116 of the pump 110 is overlayered with a conventional substance that tissue adheres poorly to, in order to lessen cell adhesion and growth onto the pump 110. Biocompatible substances having poor cellular adhesion thereto illustratively include fluoropolymers and silicone. A coating lessening cellular adhesion is helpful should an inventive pump require replacement during the course of a recipient's lifetime. Alternatively, the top surface 116 of the pump 110 is overlayered with a cloth skirt 119. The skirt 119 extends beyond the bottom surface 112 of the pump approximately 5 mm. During surgery, the pump 110 is sutured to the aorta A by means of a suture line fastening the skirt 119 to the aorta A.

In a preferred embodiment, a blood pump is formed that affords an inventive pump with sufficient stiffness to maintain a desired geometry while experiencing the various forces applied thereto by the aorta and hemodynamic pressure during operation yet is sufficiently flexible to be twisted and flexed during surgical implantation. Such properties are derived by varying the thickness 132 of the wall 114 as shown in cross-sectional views of FIGS. 9 and 10. It is appreciated that a finite point analysis of the forces exerted on an inventive pump will identify those portions requiring thickness reinforcement in order to obtain a desired overall mechanical performance. Generally, the wall 114 is thickness reinforced in the region around the top 116 of the pump 110, as well as a lesser thickening along the bottom edge 112. As such, the bottom surface 112 has a bead diameter 134 that is at least 10% greater in linear dimension than the adjacent wall cross section 136. Preferably, the bead diameter 132 is between 20% and 40% greater than the adjacent cross-sectional wall thickness 134.

Figure 8:
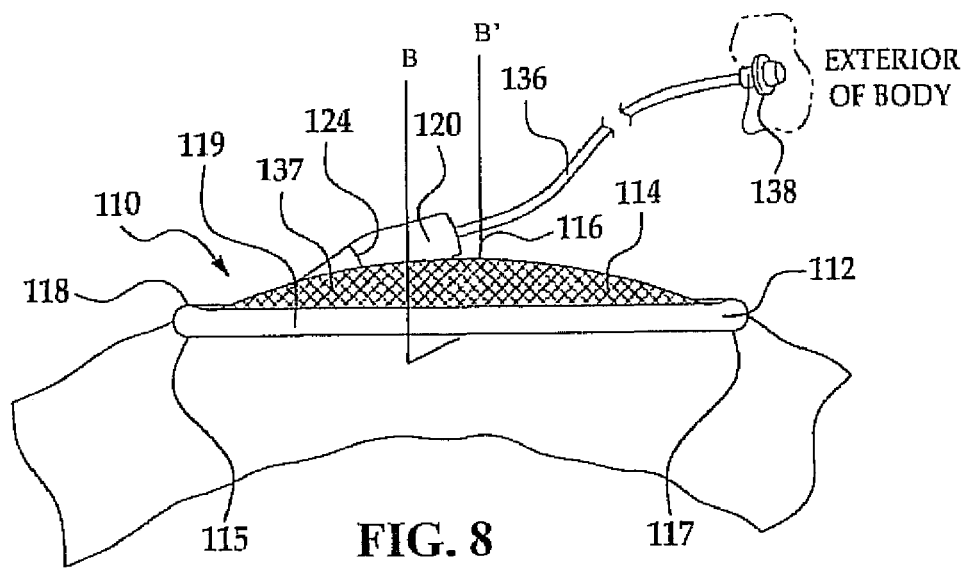
FIG. 8 is a planar view of an inventive blood pump positioned relative to a human aorta.
Figure 9:
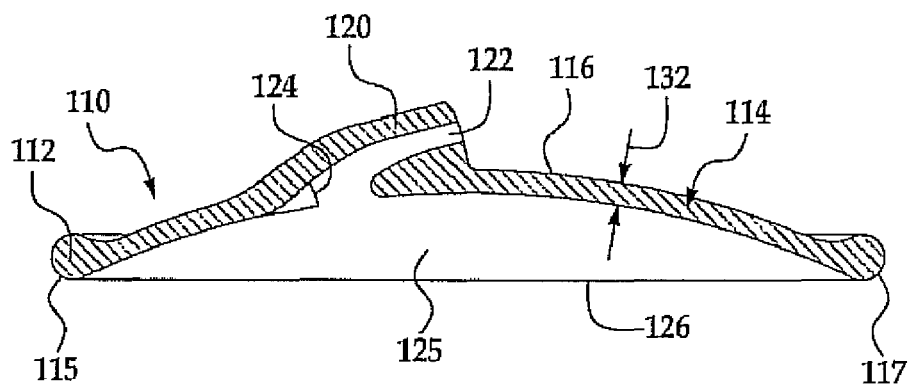
FIG. 9 is a longitudinal cross-sectional view of the inventive pump depicted in FIG. 8.
Figure 10:
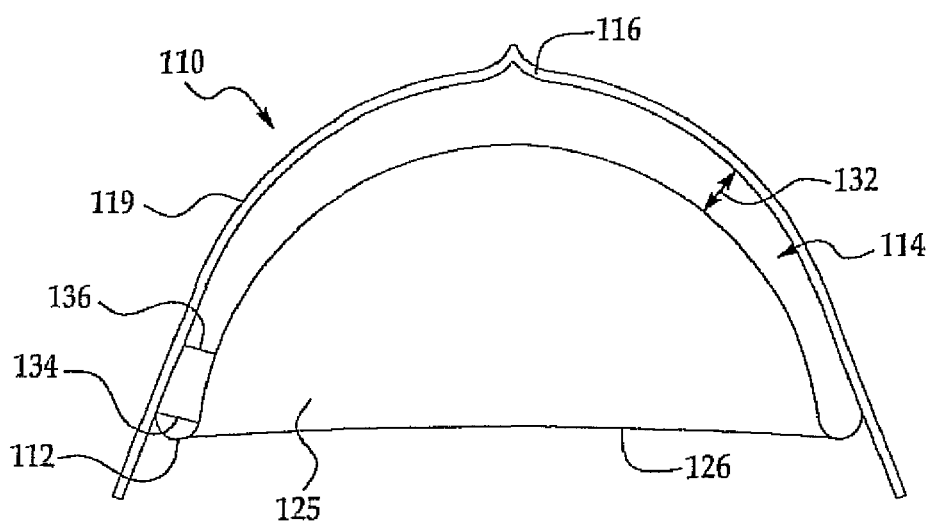
FIG. 10 is a central transverse cross-sectional view of the inventive pump of FIG. 8 along line B-B'.
Figure 11:
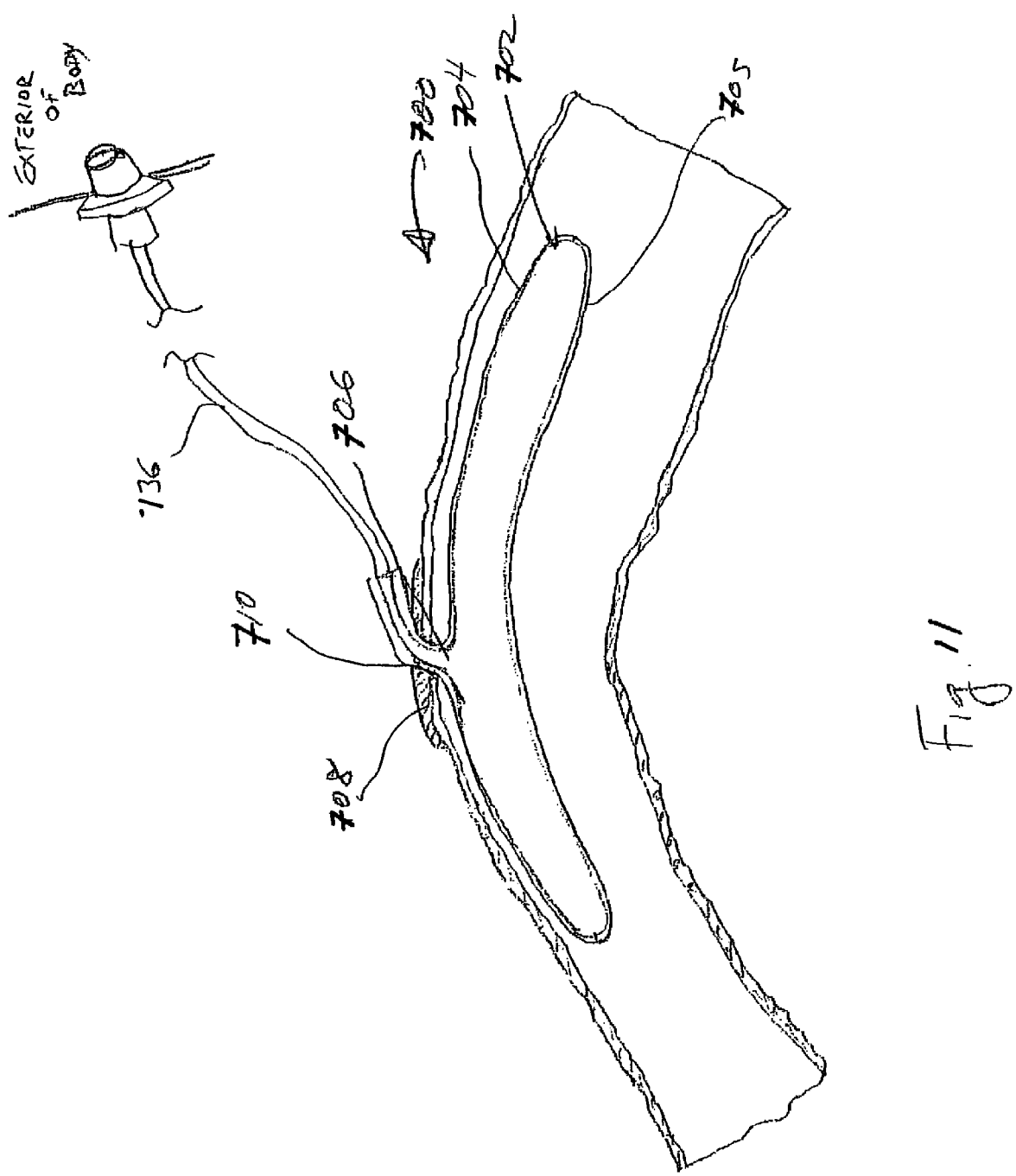
FIG. 11 is a longitudinal cross-sectional view of an alternate embodiment intra-aortic blood pump within a human aorta.

An alternate embodiment of the present invention is depicted in FIG. 11 as an intra-aortic balloon pump shown generally at 700 with like numerals corresponding to features described with respect to FIGS. 8-10. The pump 700 has an inflatable bladder 702 constructed of conventional biocompatible balloon membrane materials illustratively including urethane, polyurethane, and polyester. The bladder 702 has a curved wall 704 of inflatable material in order to follow the internal contour of the aorta A fused to an inflatable membrane 705. Preferably, the wall 704 has less elasticity than the membrane 705. An aperture 706 extends from the bladder 702. The intra-aortic pump 700 requires a small incision and less surgical time to implant, as compared to an inventive pump sutured to an aorta. Optionally, a patch 708 is sewn around the aortic lumen 710 from which the aperture 706 exits the aorta so as to better anchor the pump 700 thereto. While the formation of the bladder 702 in a seamless manner is preferred, it is appreciated that the edge fused adhesion of two sheets to form an inventive balloon is also operative herein. The curvature of the bladder 702 being created by conventional techniques including casting in a predetermined shape, embedding preshaped stiffening ribs therein, or varying the cross-sectional thickness of the balloon wall.

In operation, an inventive blood pump is connected to an external gas supply by way of aperture 122. A flexible gas tube 136 couples to the aperture 122, the gas tube 136 terminating at a percutaneous access device 138 that affords external access so that the pump 110 can be in fluid or electrical or optical communication with devices external to the patient's body. The percutaneous access device operative herein has previously been disclosed in U.S. Pat. Nos. 4,634,422 and 5,242,415. However, it is appreciated that other percutaneous access devices and other modes of surgically implanting a gas tube 136 are operative herewith. The gas tube 136 in fluid communication with a compressor for delivering a pulsatile gas flow synchronized with cardiac function as measured by an electrocardiogram (EKG). Preferably, air is pumped from the exterior by way of gas tube 136 into the interior pump volume 124 so as to cause periodic inflation of up to 150 cycles per minute. It is appreciated that gases other than air are operative with the present invention to induce pump inflation. These gases illustratively include helium, nitrogen, argon, and mixtures thereof. While these gases have lower viscosities than air, such gases necessitate tethering the recipient of an inventive blood pump implant to a compressed gas tank thereby reducing the mobility of the recipient.

Optionally, feedback sensors for the operation of an inventive blood pump are implanted within the wall 114 of the pump 110. Such sensors illustratively include a pressure transducer, an accelerometer, a strain gauge, an electrode, and species specific sensors such as pH, oxygen, creatine, nitric oxide or MEMS versions thereof. The output of such a sensor being transmitted as an electrical or optical signal via the aperture 122 through the gas tube 136 to monitoring and regulatory equipment exterior to the body of the recipient.

In constructing a blood pump for an individual, it is appreciated that improved conformality can be achieved between an inventive pump and an aorta through prior medical scans of the individual's aorta to obtain information about the anatomical characteristics of the aorta. An inventive blood pump is then selected from a number of premade geometries or custom contoured thereto.

An inventive pump displaces from about 40 to 70 cubic centimeters of blood upon inflation. In a preferred embodiment, the pump displaces from 50 to 70 cubic centimeters of blood so as to allow an individual having an inventive pump implanted an active lifestyle. Still more preferably, an inventive pump displaces from about 60 to 65 cubic centimeters of blood upon inflation thereby achieving satisfactory blood flow without occupying excess space within a chest cavity.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The apparatus and methods described herein are presently representative of preferred embodiments, exemplary, and not intended as limitations on the scope of the invention. Changes therein and other uses will occur to those skilled in the art. Such changes and other uses are encompassed within the spirit of the invention as defined by the scope of the claims.

What is claimed is:

1. An implantable aortic blood pump, comprising:
   an elongate shell having a contoured concave inner surface terminating at a peripheral side edge tapering at both ends to approximate the geometrical intersection of the elongate shell with a substantially cylindrical native human aorta; a suture flange coupled to the elongate shell;
   at least one passage integral with and through the shell to define an opening in the inner surface, the at least one passage integral with the shell and having an angle relative to the inner surface of between 5 and 30 degrees;
   an elongate flexible membrane continuously bonded to said shell adjacent to the peripheral side edge, said flexible membrane in cooperation with said shell defining an enclosed inflatable chamber in fluid communication with the at least one passage and adapted to deflect outward from said elongate shell, the shell being more rigid than the membrane;
   a stent composed of a wire-mesh material disposed between the suture flange and the shell, the stent being attached at said shell and positioned to increase shell rigidity, the stent having an expanded state that defines a substantially open cylindrical area for expansion of said flexible membrane; and
   wherein the suture flange includes a piece of sheet material shaped to seal said shell to an incised wall of a native human aorta.

2. The system of claim 1 wherein the stent is partially embedded in a wall of the shell.

3. The system of claim 1 wherein the stent is attached to an outer surface of the shell.

4. The system of claim 1 wherein the suture flange is bonded to an outer surface of the shell and is freely projecting.

5. A cardiac assist system comprising an aortic blood pump implantable in a patient aorta internal to a patient body, the pump comprising:
   an elongate shell having a contoured concave inner surface terminating at a peripheral side edge tapering at both ends to approximate the geometrical intersection of the elongate shell with a substantially cylindrical native human aorta and where the elongate shell is adapted to be joined to an interior incised wall of the patient aorta;
   at least one passage integral with and through the shell to define an opening in the inner surface, the at least one passage integral with the shell and having an angle relative to the inner surface of between 5 and 30 degrees;
   an elongate flexible membrane continuously bonded to said shell adjacent to the peripheral side edge, said flexible membrane in cooperation with said shell defining an enclosed inflatable chamber in fluid communication with the passage and adapted to deflect outward from said elongate shell;
   a suture flange;
   a stent composed of a wire-mesh material disposed between the suture flange and the shell and having an expanded state defining a substantially open cylindrical area for expansion of said flexible membrane;

the suture flange including a piece of sheet material attached to the shell and shaped to seal said shell to the incised wall of the native human aorta; and a gas tube adapted to afford fluid communication between the aortic blood pump and a region external to the patient body.

6. The system of claim 5 further comprising a percutaneous access device intermediate between the gas tube and the exterior of the patient's body.

7. The system of claim 5 further comprising a compressor in fluid communication with the gas tube for delivering a pulsatile gas flow, an energy source that powers the compressor, an air tank that supplies a gas for the pulsatile gas flow, and electronics necessary to control the operation of the system.

8. The system of claim 5 further comprising an air tank containing a supply of air communicated via the gas tube to the pump.

9. The system of claim 5 wherein the stent is partially embedded in a wall of the shell.

10. The system of claim 5 wherein the stent is attached to an outer surface of the shell.

11. The system of claim 10 wherein the suture flange is bonded to an outer surface of the shell and is freely projecting.

12. The system of claim 5 wherein the shape of the pump is custom contoured with prior medical scans of the individual's aorta and information about the anatomical characteristics of the aorta.

13. The system of claim 5 wherein the suture flange is bonded to the outer surface of the shell.

\* \* \* \* \*